United States Patent
Chi et al.

(10) Patent No.: US 9,978,142 B2
(45) Date of Patent: May 22, 2018

(54) SYSTEM AND METHOD FOR QUALITY ASSESSMENT OF OPTICAL COLONOSCOPY IMAGES

(71) Applicants: Arizona Board of Regents on Behalf of Arizona State University, SWcottsdale, AZ (US); Mayo Foundation For Medical Education And Research, Rochester, MN (US)

(72) Inventors: Changching Chi, Loton Township (TW); Nima Tajbakhsh, Tempe, AZ (US); Haripriya Sharma, Tempe, AZ (US); Suryakanth Gurudu, Phoenix, AZ (US); Jianming Liang, Scottsdale, AZ (US)

(73) Assignees: Arizona Board of Regents on Behalf of Arizona State University, Scottsdale, AZ (US); Mayo Foundation for Medical Education and Research, Rochester, MN (US)

( * ) Notice: Subject to any disclaimer, the term of this patent is extended or adjusted under 35 U.S.C. 154(b) by 33 days.

(21) Appl. No.: 15/304,927

(22) PCT Filed: Apr. 24, 2015

(86) PCT No.: PCT/US2015/027493
§ 371 (c)(1),
(2) Date: Oct. 18, 2016

(87) PCT Pub. No.: WO2015/164724
PCT Pub. Date: Oct. 29, 2015

(65) Prior Publication Data
US 2017/0186154 A1 Jun. 29, 2017

Related U.S. Application Data

(60) Provisional application No. 61/983,869, filed on Apr. 24, 2014.

(51) Int. Cl.
*G06K 9/36* (2006.01)
*G06T 7/00* (2017.01)

(52) U.S. Cl.
CPC .. *G06T 7/0012* (2013.01); *G06T 2207/10068* (2013.01); *G06T 2207/30028* (2013.01)

(58) Field of Classification Search
CPC . G06T 2207/10068; G06T 2207/30028; G06T 7/0012
See application file for complete search history.

(56) References Cited

U.S. PATENT DOCUMENTS 7,300,398 B2 * 11/2007 Chefd'hotel ............. G06T 7/33
382/128
2008/0058593 A1 3/2008 Gu et al.
(Continued)

OTHER PUBLICATIONS

International Search Report and Written Opinion dated Jul. 28, 2015 in connection with PCT/US2015/027493.
(Continued)

*Primary Examiner* — Li Liu
(74) *Attorney, Agent, or Firm* — Quarles & Brady LLP (57) ABSTRACT

A system for quality assessment of optical colonoscopy images includes an input device configured to acquire a series of images during an optical colonoscopy. A computing device is coupled in communication with the input device and configured to acquire from the input device an input image from the series of images captured during the optical colonoscopy; form a cell grid including a plurality of cells on the input image; perform an image transformation onto the input image with each cell of the plurality of cells within the cell grid; reconstruct each cell to form a reconstructed image; compute a difference image of a sum of a plurality of differences between the input image and the reconstructed image; compute a histogram of the difference image; and apply a probabilistic classifier to the histogram to calculate an informativeness score for the input image.

20 Claims, 5 Drawing Sheets

(56) References Cited

U.S. PATENT DOCUMENTS

| | | | |
|---|---|---|---|
| 2012/0316421 A1* | 12/2012 | Kumar | A61B 1/00009 600/407 |
| 2013/0039566 A1 | 2/2013 | Reznick et al. | |
| 2013/0121546 A1* | 5/2013 | Guissin | G06T 7/0012 382/128 |
| 2014/0169662 A1* | 6/2014 | Liu | G06K 9/32 382/155 |
| 2014/0219531 A1* | 8/2014 | Epstein | G01R 33/56308 382/131 |

OTHER PUBLICATIONS

Hafner, M. et al. "Computer-Assisted Pit-Pattern Classification in Different Wavelet Domains for Supporting Dignity Assessment of Colonic Polyps"; Pattern Recognition, vol. 42, Issue 6; Publication [online]. Jun. 2009 [retrieved Jul. 6, 2015]. Retrieved from the Internet: URL: http://www.researchgate.net/publication/220603177>; pp. 1-28.

Kwitt, R. et al. "Feature Extraction from Multi-Directional Multi-Resolution Image Transformations for the Classification of Zoom-Endoscopy Images"; Pattern Analysis and Applications; Publication [online]. Jan. 2009 [retrieved Jul. 11, 2015]. Retrieved from the Internet <URL: http://www.researchgate.net/publicaton/220654674>; pp. 1-12.

\* cited by examiner

SYSTEM AND METHOD FOR QUALITY ASSESSMENT OF OPTICAL COLONOSCOPY IMAGES

CROSS-REFERENCE TO RELATED APPLICATIONS

This application is a 371 application of PCT/US2015/027493 Filed Apr. 24, 2015, which claims priority to U.S. Provisional Patent Application No. 61/983,869 filed Apr. 24, 2014, the contents of which are incorporated by reference herein for all purposes.

STATEMENT REGARDING FEDERALLY SPONSORED RESEARCH

N/A

BACKGROUND

The subject matter described herein relates to systems and methods for processing images obtained during an optical colonoscopy procedure, and, more particularly, to an image quality assessment system and method to automatically evaluate the processed images and assign an informativeness score to each image.

Colorectal cancer (CRC) is the second highest cause of cancer-related deaths in the United States with 50,830 estimated deaths in 2013. A majority of these deaths may have been prevented by using a high quality screening test. More than 80% of CRC cases arise from adenomatous polyps, which are precancerous abnormal growths of the colon wall. The preferred screening method for polyp detection and removal is an optical colonoscopy (OC) procedure, during which a colonoscopist meticulously examines the colon wall using a tiny camera that is inserted and guided through the colon. The goal of an OC is to detect and remove colorectal polyps, which may be precursors to CRC. It has been shown that timely removal of polyps can significantly reduce the mortality of CRC.

However, polyp detection with an OC remains a challenging task and, as evidenced by several clinical studies, a significant portion of flat, sessile, and pedunculated polyps remain undetected during colon screening with an OC. OC as the primary modality for screening and preventing colorectal cancer is still far from ideal with polyps and cancers being missed during procedures. A Canadian study reports a 6% cancer miss-rate during colonoscopy and attributes this to the polyps that are missed due to insufficient quality of procedures. This is due to the fact that the effectiveness of a colonoscopy for polyp detection highly depends on the visibility of the images that are captured by the camera and subsequently displayed on a monitor. Therefore, higher quality images taken during a colonoscopy allow for a higher quality colonoscopy procedure. Existing methods for making objective quality assessments use a gray level co-occurrence matrix (GLCM) in the Fourier domain and/or two-dimensional (2D) discrete wavelet transform (DWT) in the spatial domain. However, these methods both fail to achieve high accuracy for a collected dataset.

Further, an OC is also an operator-dependent task wherein the quality of the examination depends on the colonoscopist's level of diligence and attentiveness during the colon examination. The quality of a colonoscopy procedure is currently assessed by measuring the total examination time. However, the total examination time is not informative enough to completely reflect the quality of a procedure. For example, a colonoscopist may spend a large amount of time in one segment of the colon but perform a quick examination in other parts of the colon. Therefore, in analyzing the metrics of the particular procedure described above, an evaluator may note the long examination time and correlate this long examination time with a thorough procedure.

Therefore there is a need for a system and associated method to overcome the inherent difficulties in assessing the quality of an examination by analyzing a length of time required to complete an examination. There is also a need for an image quality assessment for colonoscopy which provides feedback to an operator of the quality of the images taken during a colonoscopy procedure and then, subsequently, the overall quality of the procedure based on the information captured in the images.

SUMMARY

In one aspect, a system for quality assessment of optical colonoscopy images includes an input device configured to acquire a series of images during an optical colonoscopy. A computing device is coupled in communication with the input device. The computing device includes a processor platform having a processor and a memory containing instructions that, when executed by the processor, causes the processor to perform a process on each image of the series of optical images comprising: acquiring from the input device an input image from the series of images captured during the optical colonoscopy; forming a cell grid including a plurality of cells on the input image; performing an image transformation of the input image with each cell of the plurality of cells within the cell grid; reconstructing each cell to form a reconstructed image; computing a difference image of a sum of a plurality of differences between the input image and the reconstructed image; computing a histogram of the difference image; and applying a probabilistic classifier to the histogram to calculate an informativeness score for the input image.

In one aspect, a method for providing an informativeness assessment of an image of a video sequence recorded during an optical colonoscopy, includes obtaining from a camera an input image captured during an optical colonoscopy. A cell grid including a plurality of cells is formed on the input image. An image transformation is performed of the input image with each cell of a plurality of cells within the cell grid. Each cell is reconstructed to form a reconstructed image. A difference map is computed as an absolute difference between the input image and the reconstructed image, wherein the difference map represents an amount of reconstruction error between the input image and the reconstructed image. A histogram is computed for the difference map corresponding to the input image. An informativeness score is obtained for the input image by applying a probabilistic classifier to the histogram.

The foregoing and other aspects and advantages of the disclosure will appear from the following description. In the description, reference is made to the accompanying drawings which form a part hereof, and in which there is shown by way of illustration certain embodiments. Such embodiments do not necessarily represent the full scope of the disclosure, however, and reference is made therefore to the claims herein for interpreting the scope of the disclosure.

DETAILED DESCRIPTION

The present disclosure describes embodiments that overcome the aforementioned drawbacks by providing a system and an associated method for automatically assigning an informativeness score for one or more images of a sequence of images of a video recorded during an OC procedure.

Figure 1:
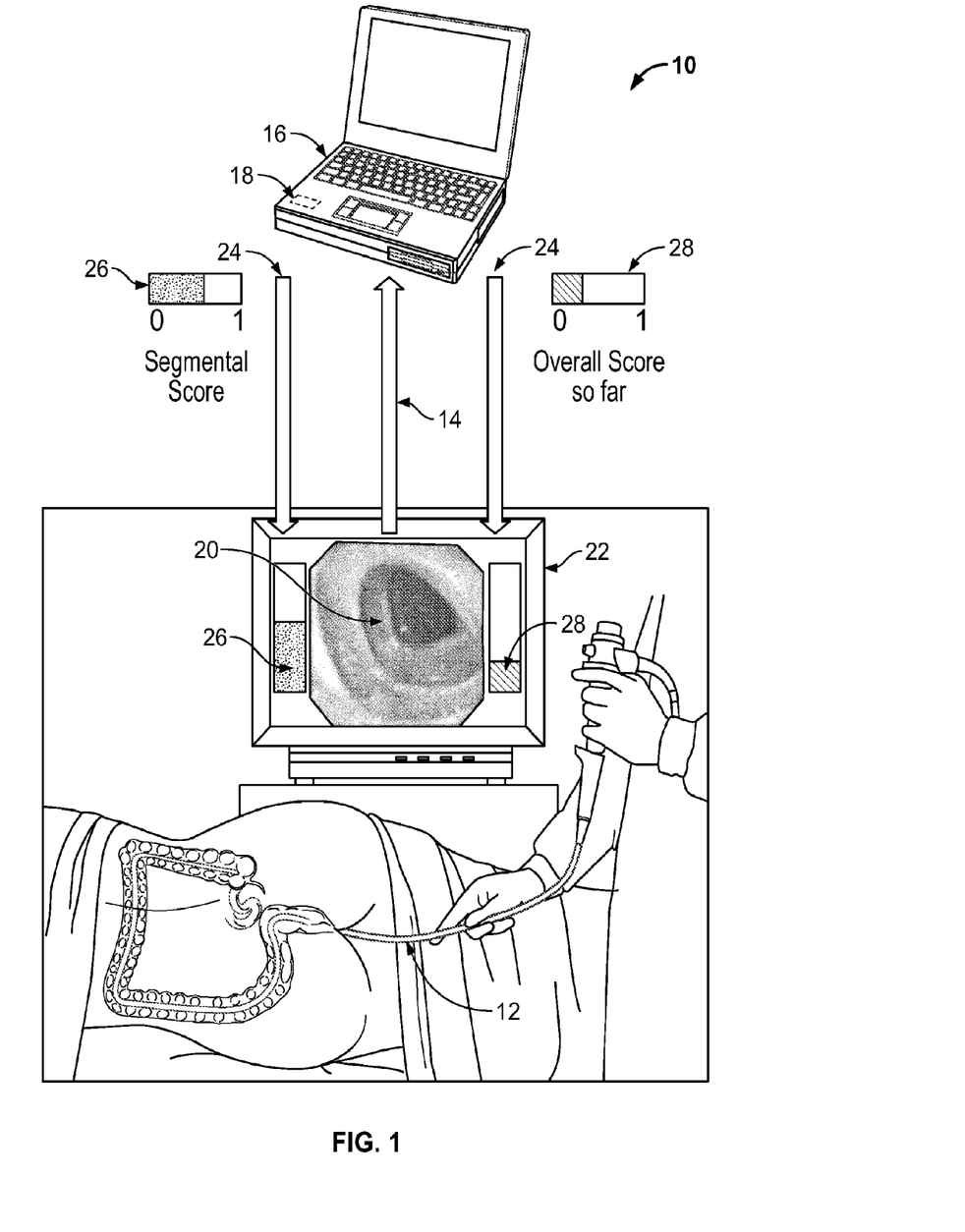
FIG. 1 is a schematic view of an exemplary system for automatic quality assessment of an optical colonoscopy image in accordance with the present disclosure.

Referring to FIG. 1, a system 10 for performing an OC procedure is shown. In this embodiment, a colonoscopist or other medical professional inserts an input device, such as a small video camera 12, into a patient's colon. The video camera 12 captures and transmits one or more images 14, such as a sequence of images 14, to a computing device 16 of the system 10 for processing. More specifically, the computing device 16 may be implemented by one or more circuits, programmable processors, application specific integrated circuits (ASICs), programmable logic devices (PLDs) and/or field programmable logic devices (FPLDs), and/or one or more additional and/or alternative devices. The computing device 16 also includes a tangible and/or non-transitory computer readable medium such as a memory, DVD, CD, etc. storing software and/or firmware. For example, the computing device 16 of FIG. 1 includes a processor platform 18 in signal communication with the video camera 12 to receive from the video camera 12 image signals representing images 14 captured during the OC procedure. The computing device 16 processes each of one or more of the images 14 to create a corresponding reconstructed image 20. The computing device 16 is coupled in communication with a display 22 that displays the processed or reconstructed images 20 to provide real-time images of a patient's colon. The display 22 may be, for example, a computer monitor, a television screen, a display of a hand-held device (e.g., a smartphone, a laptop, a tablet, etc.) and/or any other type of display. The display 22 can also display informativeness scores for a current procedure. As each image 14 is captured, the computing device 16 processes the image 14 and then assigns each image 14 an informativeness score or an image quality score 24 between 0 and 1 with 0 being a non-informative image and 1 being an informative image. These informativeness scores 24 can then be used in calculating a segmental score 26 or an overall score 28.

Summary statistical analysis of the informativeness scores 24 for the images 14 captured between time $t_1$ and time $t_2$ determines the informativeness of the video images over the past t seconds. This score is referred to as the segmental score 26. The computing device 16 can be programmed to review the segmental score 26 over a predetermined period of time. For example, the computing device 16 can be programmed to display on the display 22 the segmental score 26 for the previous ten minutes and to continually update the segmental score 26 over a time period. The segmental score 26 can be displayed on the display 22 in real-time. This allows a colonoscopist or other user to see real-time feedback of his/her performance for a specified period of time. Given the segmental feedback, a colonoscopists may decide to go back and re-visit the area for which the segmental score has been poor, because poor-quality inspection in that area may have missed a polyp.

The segmental score 26 differs from the overall score 28 which is measured by performing summary statistical analysis of the informativeness scores 24 computed from time 0 to the current time. The overall score 28 allows a colonoscopist or other user to see real-time feed back of his/her entire procedure from the beginning of the procedure to the current time. The system 10 can continually show an updated segmental score 26 and the overall score 28 on the display 22 to inform the colonoscopist of his/her quality of work during a procedure. The system 10 also reports the informativeness scores 24 including one or more segmental scores 26 and/or the overall score 28 at the end of the procedure which can then be used for quality monitoring purposes. The desire to achieve high overall scores on examination reports will discourage a colonoscopist from performing hasty examinations and encourage the colonoscopist to dedicate more time and effort during colonoscopy procedures. The segmental score 26 is shown to the colonoscopist to alert the occurrence of a hasty examination or onset of a drop in the overall score 28. This allows the colonoscopist to respond by slowing down and spending more time during the examination to take higher quality video images of a patient's colon.

Evaluating an examination based on the quality of the images taken and not on the overall time also encourages higher quality examinations rather than merely longer examinations that may still be of lower quality. For example, a colonoscopist may spend a large amount of time in one segment of the colon but perform a quick examination in other parts of the colon. Therefore, in analyzing the metrics of the particular procedure described above, an evaluator may note the long examination time and correlate this long examination time with a thorough procedure. However, because of the example described above, a better metric for analyzing the quality of a colonoscopy procedure would be to review the quality of the images or video taken during an examination. Colonoscopists can achieve a higher segmental or overall score by focusing on the quality of images taken during the procedure to ensure that the images are of good quality and sharpness. Thus, because the colonoscopist can view real time feedback of his/her examination, the colonoscopist is able to adjust during an examination rather than having to wait for feedback after an examination. Accordingly, a colonoscopist who focuses on taking better quality images during a colonoscopy will be more likely to detect polyps and this results in a better, more thorough colonoscopy procedure for the patient.

Figure 2:
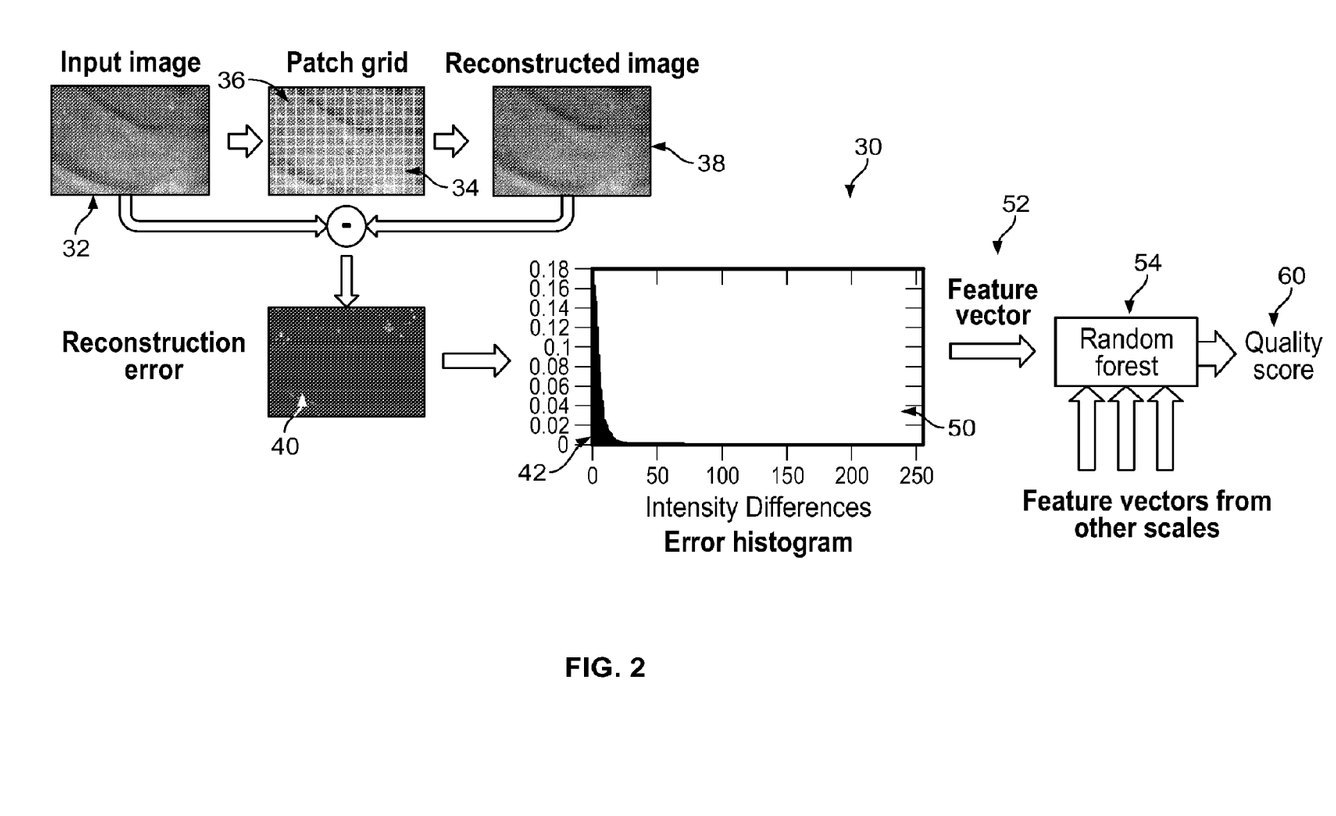
FIG. 2 is a flowchart for an exemplary method for automatically assigning an informativeness assessment of a video sequence during a portion of an optical colonoscopy procedure in accordance with the present disclosure.

Referring now to FIG. 2, a method for providing an informativeness assessment 30 of an image of a video sequence recorded during an optical colonoscopy begins with obtaining an input image 32. In this method, the input image 32 captured during the optical colonoscopy is obtained from the video camera 12 or other suitable input device. A cell grid 34 including a plurality of cells 36 is placed or formed on the input image 32. In one embodiment, the system 10 can use a cell grid 34 having a predetermined grid size such as, for instance, an 8×8-cell or 16×16-cell grid size. In a particular embodiment, additional cells 36 can be added to cell grid 34 as needed to cover the entire input image 32 if desired. Therefore, in certain embodiments, the size of the input image 32 determines the number of cells 36 required in a horizontal direction and/or a vertical direction of the cell grid 34. In an alternative embodiment, the system 10 fixes the number of cells 36 in the horizontal direction and/or the vertical direction. In this instance, the size of the cell grid 34 is automatically determined based on the size of the input image 32. Thus, a larger input image 32 necessarily requires a larger cell grid 34 to completely cover the input image 32. Once the cell grid 34 is calculated and formed, the system 10 applies a 2D Discrete Cosine Transform (DCT) on each cell 36 within the cell grid 36 and then reconstructs the cell 36 using a subset of dominant, low frequency DCT coefficients. The reconstructed cells 36 are then repositioned to form a reconstructed image 38.

The system 10 can then compute a difference image or map 40 as an absolute difference between the input image 32 and the reconstructed image 38. This difference map 40 represents an amount of reconstruction error 42 between the input image 32 and the reconstructed image 38. In general, the difference map 40 contains low levels of reconstruction error for a non-informative image and higher levels of reconstruction error for an informative image.

The system 10 can use the information within the difference map 40 to discriminate between the non-informative images and the informative images. In one embodiment, the system 10 can perform this analysis by computing a histogram 50 of the difference map 40 because it is computationally efficient, it is independent of the size of the input images 32, and it requires a fixed number of bins to represent the information hidden in the difference map 40. For gray scale colonoscopy images, the histogram 50 contains only 256 bins, which efficiently represents the information content of the difference map 40. Thus, the histogram 50 can be computed for each difference map 40 corresponding to a different input image 32. Each computed histogram 50 can be viewed as a feature vector 52 corresponding to the input image 32. The resulting feature vectors 52 are then used to train a probabilistic classifier 54 for computing and outputting an informativeness score 60. Thus, the set of histograms 50 can be collected and a probabilistic classifier 54 can be applied to assign a probabilistic output for each input image 32. In this embodiment, the probabilistic output of the classifier 54 for each image is the informativeness score 60, which ranges between values of 0 and 1. A quality score 60 of 0 indicates an image of the worst possible quality and a quality score 60 of 1 indicates an image of the best possible quality.

In one embodiment, a random forest classifier can be used as the classifier 54 because of its capability to produce accurate probabilistic outputs. In alternative embodiments, any other suitable classification technique that can output probabilistic scores, such as a support vector machine, can also be employed.

The accuracy of the method described above can be further enhanced by extracting more features from the difference map 40. In one embodiment, the system 10 can scale down the input image 32 by a factor of 2, one or more times. For example, the system 10 can resize an original 512×512 input image to a 256×256 image, a 128×128 image, and then further to a 64×64 image. The system 10 can then perform the above-mentioned method for each of these 4 images. This results in 4 histograms that are further concatenated to form a feature vector 52 of 1024 elements (4×256). The new feature vectors 52 are then passed to a probabilistic classifier 54, such as a random forest classifier, for image information assessment.

The method for providing an informativeness assessment 30 of an image as shown in FIG. 2 may be implemented using a program for execution by one or more processors such as the processor platform 18 described in conjunction with FIG. 1. However, the entire program and/or portions of the program could be executed by one or more additional and/or alternative devices. The program(s) may be stored on a tangible computer readable medium such as a CD-ROM, a hard drive, a flash drive, a digital versatile disk (DVD), or a memory employed by the processor(s).

As mentioned above, the exemplary method of FIG. 2 may be implemented using computer readable instructions stored on a tangible computer readable medium. As used herein, a tangible computer readable medium is not a propagating signal. Additionally or alternatively, the method of FIG. 2 may be implemented using computer readable instructions stored on a non-transitory computer readable medium such as a hard drive, a flash drive, a CD-ROM, and/or any other non-transitory storage media in which information is stored. As used herein, a non-transitory computer readable medium is not a propagating signal.

In some embodiments, the processor platform 18 is implemented via one or more general-purpose processors, processor cores, microcontrollers, and/or one or more additional and/or alternative processing devices. The processor platform 18 of FIG. 1 includes a programmable, general purpose processor to execute coded instructions within a random access memory and/or a read-only memory. The coded instructions may include instructions executable to implement the method of FIG. 2. The processor may be any type of processing device, such as a processor core, a processor and/or a microcontroller. The processor is in communication with the random access memory and the read-only memory via a communications bus. The random access memory may be implemented by any type of random access memory device such as, for example, DRAM, SDRAM, etc. The read-only memory may be implemented by any type of memory device such as, for example, flash memory. In some embodiments, the processor platform 18 includes a memory controller to control access to the random access memory and/or the read-only memory. The processor platform 18 of FIG. 1 includes an interface that may be implemented by an interface standard such as, for example, an external memory interface, a serial port, a general-purpose input/output, and/ or any other type of interface standard. The processor platform 18 of FIG. 1 includes at least one input device and at least one output device coupled to the interface.

Specific examples are provided below, illustrative of the above-described image assessment method. These examples are offered for illustrative purposes only, and are not intended to limit the scope of the present disclosure in any way. Indeed, various modifications of the disclosure in addition to those shown and described herein will become apparent to those skilled in the art from the foregoing description and the following example and fall within the scope of the appended claims.

Example

A database of colonoscopy procedure videos was used to evaluate the methodology described in the current disclosure. Images were taken from each of the sample videos and an image quality assessment was performed on each of the images using the current method and two conventional assessment methods. A first conventional assessment method uses a gray level co-occurrence matrix in the Fourier domain to assess image quality ("the GLCM method"). A second conventional assessment method uses 2D discrete wavelet transform in the spatial domain ("the DWT method"). Each of the three image quality assessment methods was applied to the images extracted from the sample videos.

Figure 3:
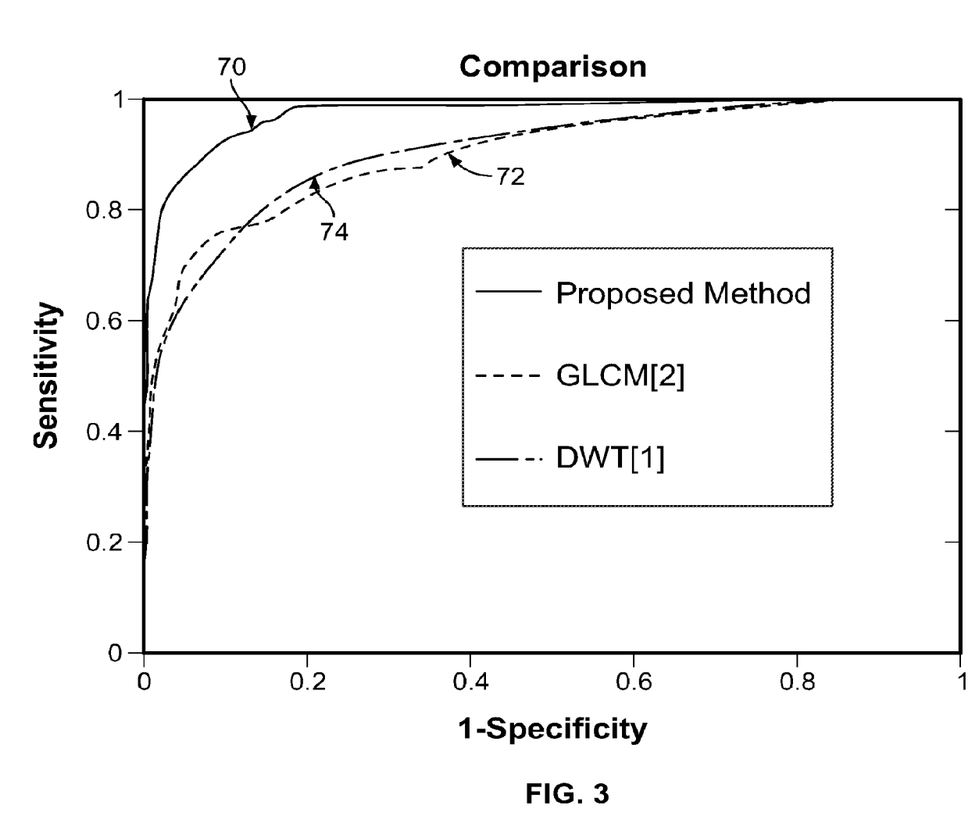
FIG. 3 is a graph showing a comparison of an exemplary method of the present disclosure against two conventional methods for objectively assessing a quality of an optical colonoscopy procedure.

FIG. 3 shows a comparison of the three methods. As seen in FIG. 3, at a low false positive rate, the ROC curve for the proposed method 70 achieves a significantly higher sensitivity than either the GLCM method 72 or the DWT method 74.

Figure 4:
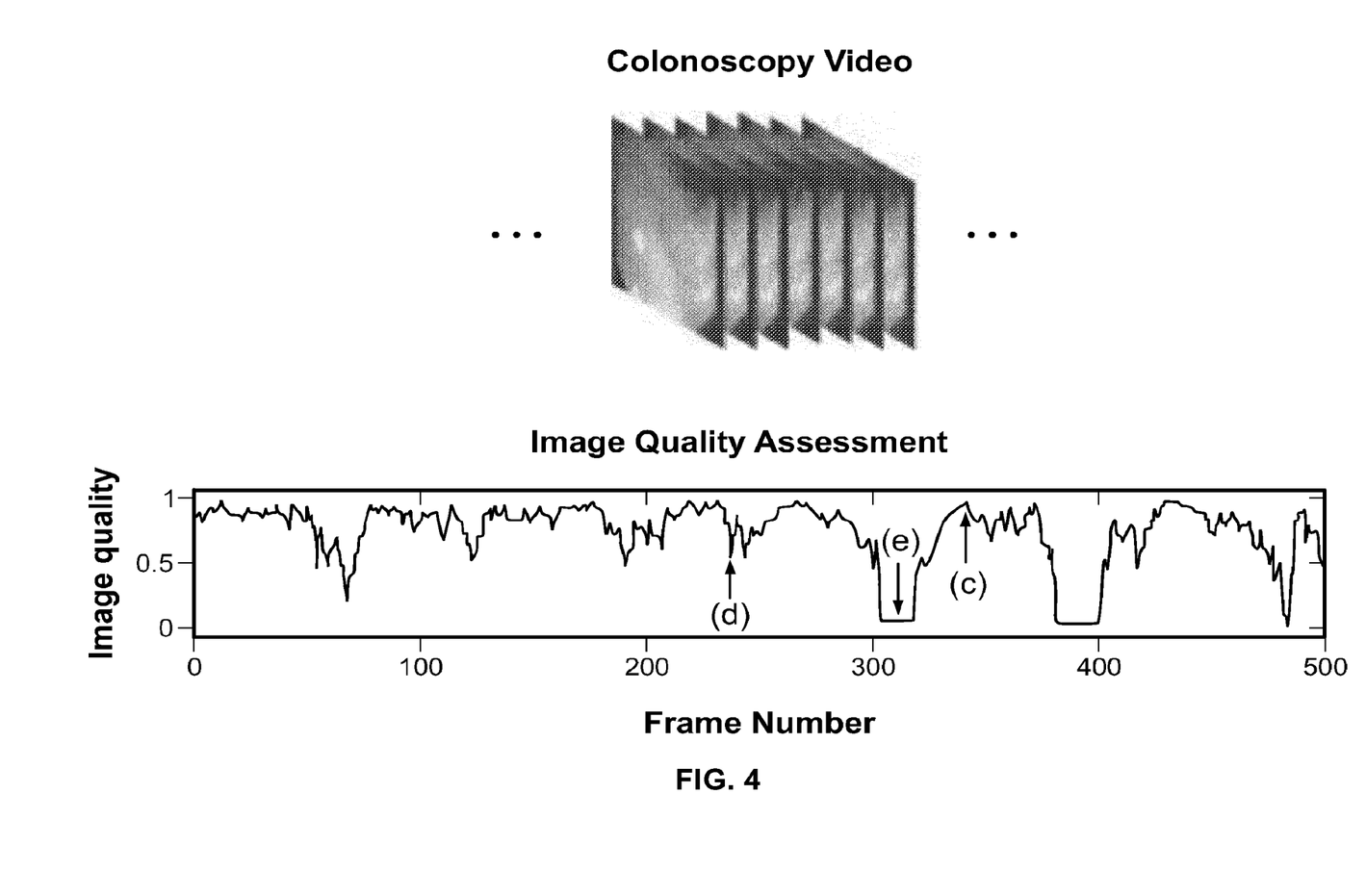
FIG. 4 is a graph showing a sample image quality assessment applied to a portion or segment of a video recording of an optical colonoscopy procedure in accordance with the present disclosure.

FIG. 4 includes a graph showing a sample image quality assessment applied to a portion or a segment of a video recording of an optical colonoscopy procedure in accordance with the present disclosure. FIG. 4 illustrates that a video can be broken up into hundreds of individual image frames for processing and analysis. Here, the sample colonoscopy video was broken into individual image frames and sample image frames (c), (d), and (e) were chosen because they illustrated the varying degrees of image quality that may be produced during a video recording of a colonoscopy procedure. Image frame (c) is illustrative of an informative image due to its high image quality or informativeness value. Image frame (d) is illustrative of an ambiguous image due to its average image quality or informativeness value. Image frame (e) is illustrative of a non-informative image due to its low image quality or informativeness value.

Figure 5:
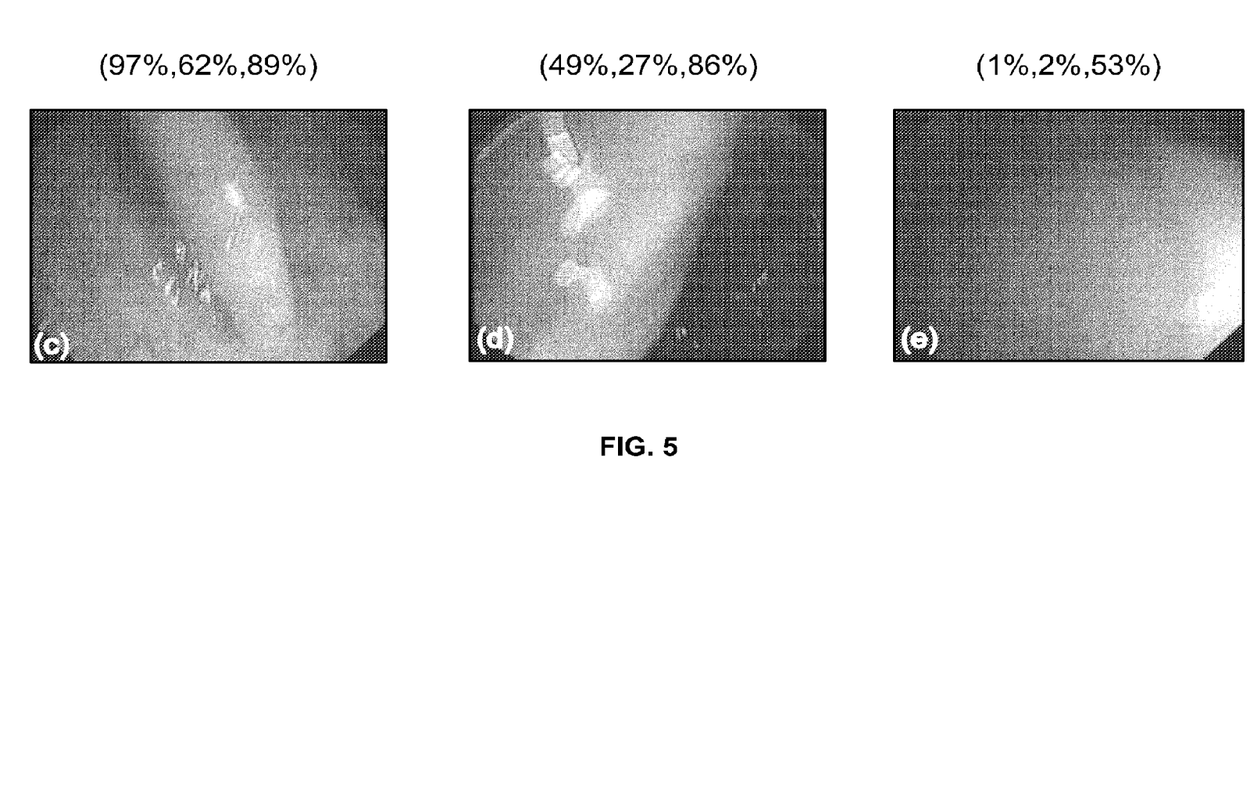
FIG. 5 is an illustration showing examples of an informative image (c), an ambiguous image (d), and a non-informative image (e) along with image quality assessment scores for each image using an exemplary method of the present disclosure and two conventional methods for objectively assessing a quality of an optical colonoscopy procedure.

FIG. 5 shows three image frames of the video of FIG. 4 and indicates the corresponding informativeness score or quality assessment score assigned by the three image quality assessment methods, namely, the proposed method 70, the GLCM method 72 and the DWT method 74. As shown in FIG. 5, the first image frame, image frame (c), is a good quality image that clearly shows portions of a colon. This image is considered an informative image. Thus, one would expect a high informativeness score for this type of image. Using the proposed method 70, image frame (c) is assigned an informativeness score of 0.97 which is in line with what would be expected for such a high quality image. However, the GLCM method 72 assigns an informativeness score of 0.62 and the DWT method 74 assigns an informativeness score of 0.89. Thus, the informativeness scores assigned using the conventional assessment methods are not as accurate as the informativeness score assigned using the proposed method 70.

The second image frame, image frame (d), shows a lower quality image that shows portions of a colon but is clearly more blurry than the image shown in image frame (c). This image is considered an ambiguous image because information provided in the image is ambiguous. The image neither provides a high level of information nor is the image completely non-informative. Therefore, one would expect a corresponding lower informativeness score than that of an informative image. The proposed method 70 falls in line with expectations and assigns an informativeness score of 0.49. However, the GLCM method 72 assigns an informativeness score of 0.27. This score is too low and, thus, inaccurate because portions of the colon can still be seen in this image. This image is just a bit blurry and lacks sharpness but not sufficiently so to warrant an informativeness score of 0.27. The DWT method 74 assigns an informativeness score of 0.86 to image frame (d). Thus, according to the DWT method 74, the quality of image frame (d) is approximately equal to the quality of image frame (c) which is false because image frame (d) is significantly less sharp than image frame (c). Therefore, an informativeness score of 0.86 would not fall in line with expected human perception of this image frame.

The third image frame, image frame (e), is a poor quality image. This image is considered a non-informative image because it is very dark, out of focus, and does not provide useful information for the colonoscopist. The darkness of the image would not be helpful to a colonoscopist in attempting to detect polyps. Therefore, one would expect a very low informativeness score. The proposed method 70 assigns an informativeness score of 0.01 which falls in line with expectations for such a low quality image. The GLCM method 72 assigns an informativeness score of 0.02 which is low but not as low and as accurate as the proposed method 70. However, the DWT method 74 assigns an informativeness score of 0.53 which is quite inaccurate for such a non-informative image.

Thus, throughout the range of informative, ambiguous and non-informative images, the proposed method 70 provides the most accurate informativeness scores for each of the three different categories of image quality assessments. The informativeness scores assigned using the proposed method 70 are more inline with human perception than the informativeness scores assigned by the GLCM method 72 and the informativeness scores assigned by the DWT method 74.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Reference throughout this specification to "one embodiment" or "an embodiment" may mean that a particular feature, structure, or characteristic described in connection with a particular embodiment may be included in at least one embodiment of claimed subject matter. Thus, appearances of the phrase "in one embodiment" or "an embodiment" in various places throughout this specification is not necessarily intended to refer to the same embodiment or to any one particular embodiment described. Furthermore, it is to be understood that particular features, structures, or characteristics described may be combined in various ways in one or more embodiments. In general, of course, these and other issues may vary with the particular context of usage. Therefore, the particular context of the description or the usage of these terms may provide helpful guidance regarding inferences to be drawn for that context.

The foregoing description of embodiments and examples has been presented for purposes of illustration and description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent devices by those of ordinary skill in the art. Rather, it is hereby intended the scope be defined by the claims appended hereto. Additionally, the features of various implementing embodiments may be combined to form further embodiments. As used herein, the word "exemplary" means serving as an example, instance, or illustration. Any aspect or embodiment described herein as "exemplary" is not necessarily to be construed as preferred or advantageous over other aspects or embodiments.

What is claimed is:

1. A system for quality assessment of optical colonoscopy images, the system comprising:
   an input device configured to acquire a series of images during an optical colonoscopy; and
   a computing device coupled in communication with the input device, the computing device including a processor platform comprising: a processor; and a memory containing instructions that, when executed by the processor, causes the processor to perform a process on each image of the series of optical images comprising:
   acquiring from the input device an input image from the series of images captured during the optical colonoscopy;
   forming a cell grid including a plurality of cells on the input image;
   performing an image transformation of the input image with each cell of the plurality of cells within the cell grid;
   reconstructing each cell to form a reconstructed image;
   computing a difference image of a sum of a plurality of differences between the input image and the reconstructed image;
   computing a histogram of the difference image; and
   applying a probabilistic classifier to the histogram to calculate an informativeness score for the input image.

2. The system of claim 1, wherein the input device comprises a video camera.

3. The system of claim 1 wherein the probabilistic classifier is a random forest classifier.

4. The system of claim 1, further comprising a display in communication with the computing device to display the informativeness score in real-time.

5. The system of claim 4, wherein the informative score includes at least one of a segmental score and an overall score.

6. The system of claim 1, wherein the memory contains instructions that, when executed by the processor, causes the processor to perform an image transformation of the input image with each cell within the cell grid by applying by the computing device a 2D Discrete Cosine Transform (DCT) on each cell.

7. The system of claim 1, wherein the memory contains instructions that, when executed by the processor, causes the processor to reconstruct each cell to form a reconstructed image by reconstructing each cell using a subset of dominant, low frequency DCT coefficients and repositioning each reconstructed cell to form the reconstructed image.

8. The system of claim 1, wherein the memory contains instructions that, when executed by the processor, causes the processor, with information within the difference map, to discriminate between non-informative images and informative images.

9. The system of claim 8, wherein the memory contains instructions that, when executed by the processor, causes the processor to analyze the information in the difference map.

10. A method for providing an informativeness assessment of an image of a video sequence recorded during an optical colonoscopy, said method comprising:
    obtaining from a camera an input image captured during an optical colonoscopy;
    forming a cell grid including a plurality of cells on the input image;
    performing an image transformation of the input image with each cell of the plurality of cells within the cell grid;
    reconstructing each cell to form a reconstructed image;
    computing a difference map as an absolute difference between the input image and the reconstructed image, wherein the difference map represents an amount of reconstruction error between the input image and the reconstructed image;
    computing a histogram for the difference map corresponding to the input image; and
    obtaining an informativeness score for the input image by applying a probabilistic classifier to the histogram.

11. The method of claim 10, wherein forming a cell grid including a plurality of cells on the input image comprises automatically determining a size of the cell grid based on a size of the input image.

12. The method of claim 10, wherein performing an image transformation of the input image with each cell within the cell grid comprises applying by a computing device a 2D Discrete Cosine Transform (DCT) on each cell of the plurality of cells.

13. The method of claim 10, wherein reconstructing each cell to form a reconstructed image comprises reconstructing each cell using a subset of dominant, low frequency DCT coefficients and repositioning each reconstructed cell to form the reconstructed image.

14. The method of claim 10, further comprising, with information within the difference map, discriminating between non-informative images and informative images.

15. The method of claim 14, wherein, with information within the difference map, discriminating between non-informative images and informative images comprises analyzing the information in the difference map.

16. The method of claim 10, further comprising:
    collecting a set of histograms; and
    applying a probabilistic classifier to assign a probabilistic output for each input image.

17. The method of claim 10, wherein the classifier includes a random forest classifier.

18. The method of claim 10, further comprising calculating a segmental score as a summary statistical value of a plurality of informativeness scores averaged between a first time, $t_1$, and a second time, $t_2$.

19. The method of claim 10, further comprising calculating an overall score as a summary statistical value of a plurality of informativeness scores averaged between a first time, $t_1$, where $t_1$ is zero, and a second time, $t_2$, wherein $t_2$ is a current time.

20. The method of claim 10, further comprising displaying on a display in communication with the computing device the informativeness score in real-time.

* * * * *